US005299119A

United States Patent [19]
Kraf et al.

[11] Patent Number: 5,299,119
[45] Date of Patent: Mar. 29, 1994

[54] AUTONOMIC NEUROPATHY DETECTION AND METHOD OF ANALYSIS

[75] Inventors: Teri J. Kraf, Point Pleasant, N.J.; William R. Frisbie, Sag Harbor, N.Y.; Allan Rosner, East Patchogue, N.Y.

[73] Assignee: Qmed, Inc., Clark, N.J.

[21] Appl. No.: 626,710

[22] Filed: Dec. 14, 1990

Related U.S. Application Data

[63] Continuation-in-part of Ser. No. 376,472, Jul. 6, 1989, abandoned.

[51] Int. Cl.$^5$ .................... G06F 15/42; G06G 7/60
[52] U.S. Cl. .................... 364/413.06; 364/413.02; 364/413.03; 364/413.05; 128/695; 128/696; 128/701; 128/702
[58] Field of Search .................... 364/413.06, 413.02, 364/413.03, 413.05; 128/695, 696, 701, 702

[56] References Cited

U.S. PATENT DOCUMENTS

| | | | |
|---|---|---|---|
| 3,267,934 | 8/1966 | Thornton | 128/702 |
| 3,613,670 | 8/1975 | Edenhofer | 128/701 |
| 4,679,144 | 7/1987 | Cox et al. | 128/710 |
| 4,922,930 | 5/1990 | Adkins et al. | 128/419 |
| 4,960,129 | 10/1990 | dePaola et al. | 128/695 |
| 4,982,738 | 1/1991 | Griebel | 128/670 |

OTHER PUBLICATIONS

Ezenwa et al. "Automated Autonomic Nervous System Analysis System", IEEE 1988, part 3 of 4, 1210-11.
Bernardi et al., "Heart Rate–Respiration Relationship Computerized Method for Early Assessment of Cardiac Autonomic Damage in Diabetic Patients" Act Cardiologic, vol. XLI, 1986, pp. 197-206.
"Sensitivity of R-R Variation and Valsalva Ratio in Assessment of Cardiovascular Diabetic Autonomic Neuropathy" Diabetes Care, vol. 10, No. 6, Nov.-Dec. 1987, pp. 735-740.
"R-R Interval Studies: A Simple Office Protocol for Evaluation of Cardiac Neuropathy". Diabetes Care vol. 7, No. 5, Sep.-Oct. 1984, pp. 510-512.
"An Improved Method for Measuring Heat Rate Variability: Assessment of Cardiac Autonomic Function." Diametrics. Sep. 1984, pp. 855-861.
Pro Sci Card by Pro Science (West Germany) (1989).
"Autonomic Neuropathy in an Alcoholic Population", Postgraduate Medical Journal 1987, 63:1033-1036.
"Systemic Sclerosis: Another disease with autonomic dysfunction", Letter from the American Neurological Association, 1988, 421-422.
"Autonomic Neuropathy and HIV Infection":, Lancet, 1987, Oct. 17:915.
"Autonomic Neuropathy in AIDS", Lancet, 1987, Aug. 8:343-344.
"Somatic and Autonomic Function in Progressive Autonomic Failure and Multiple System Atrophy", Annals of Neurology 1987; vol. 22 6:692-699.
"Disorders of the Autonomic Nervous System: Part I. Pathophysiology and Clinical Features", Annals of Neurology 1987; vol. 2, 6:419-426.
"The Value of Cardiovascular Autonomic Function Tests: 10 Years Experience in Diabetes", Diabetes Care 1985; vol. 8, No. 5, 491-497.

*Primary Examiner*—Roy N. Envall, Jr.
*Assistant Examiner*—Gita Shingala
*Attorney, Agent, or Firm*—Roylance, Abrams, Berdo & Goodman

[57] ABSTRACT

A non-invasive, programmable cardio-respiratory monitoring system for performing automated autonomic nervous system function tests by monitoring and analyzing EKG signals in relation to specific paced breathing and/or posture regimens, and immediately computing and disclosing the test results automatically upon completion of one or all of the tests. The accuracy of these tests, which are currently being performed manually and/or with multiple components, is greatly improved bt the invention's capability to issue automated audio-visual instructions to the patient, to analyze any major peak of the QRS complex for determining heart rate variation, to discriminate between normal and abnormal EKG signals, and to edit the automated test results to enhance the validity of the test results.

43 Claims, 9 Drawing Sheets

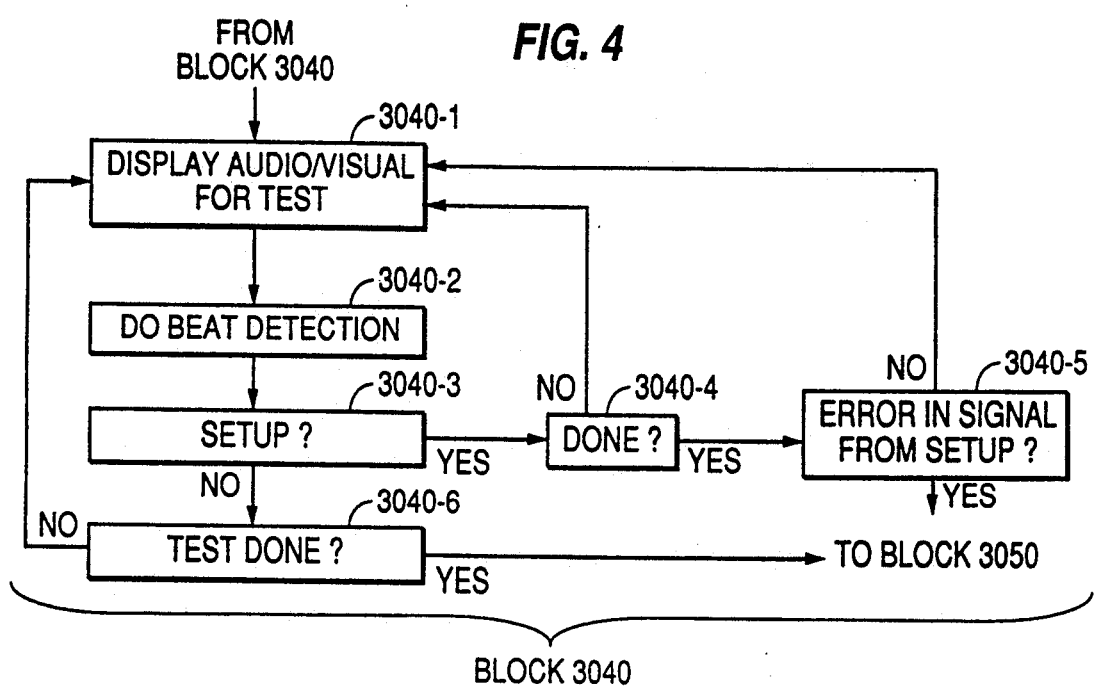
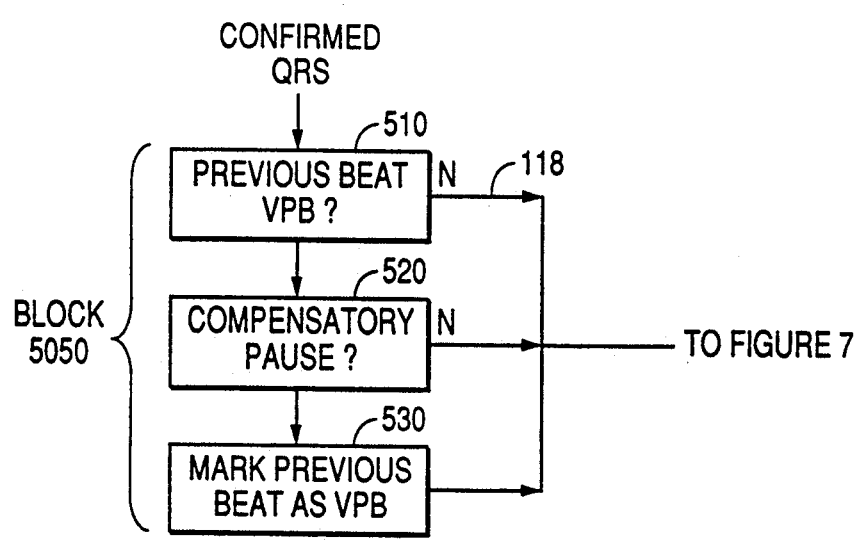

– 5,299,119 –

AUTONOMIC NEUROPATHY DETECTION AND METHOD OF ANALYSIS

REFERENCE TO RELATED APPLICATION

This application is a continuation-in-part of our co-pending U.S. patent application Ser. No. 07/376,472, filed Jul. 6, 1989, now abandoned the entire disclosure of which is hereby incorporated by reference as if here set forth in full.

FIELD OF THE INVENTION

In summary, this invention adopts the heart monitor of U.S. Pat. No. 4,679,144 to Cox et al (commonly owned with the present invention), and uses the medical teaching that patients with autonomic nervous system dysfunction such as in diabetics do not exhibit certain normal correlations of heart rate and breathing which can be ascertained by this greatly improved and highly reliable portable diagnostic device for noninvasively evaluating the functioning status of the autonomic nervous system.

BACKGROUND OF THE INVENTION

The heart monitoring device described in U.S. Pat. No. 4,679,144 to Cox et al is capable of performing continuous, real-time analyses of EKG information derived from the patient which portend underlying cardiac complications resulting from occluded coronary arteries or dysfunctional heart muscle. Due to its programmable capabilities, the heart monitoring device can further instruct the patient on the manner of cardiac treatment based on its analyses.

This invention, which is used for the evaluation of autonomic nervous system function, incorporates the real-time heart monitoring capabilities described in the above patent but extends its capabilities to include the evaluation of cardiovascular responses to predetermined breathing and/or posture regimens. This invention also includes an automated method for externally regulating these regimens by means of audio-visual instructions in order to accurately correlate cardiovascular responses to specific stimuli such as respiration and/or posture.

This invention, for the evaluation of autonomic nervous system function, incorporates the portable, self-contained real-time digital heart monitoring device and its capabilities of the Cox '144 patent, specifically its real-time digital monitoring, recording and storing capabilities of electrocardiographic signals, but extends its capabilities to include the evaluation of the cardiovascular responses to predetermined breathing and/or posture regimens.

The cardio-respiratory digital analyses, computations, audio-visual cues for accurately performing the breathing and/or posture regimens, data transfer and data editing capabilities are unique to this invention. The cardio-respiratory analyses were not applicable and are not capable of being performed by the Cox '144 invention because of the different objectives and methodologies of each invention. The computations referred to as "autonomic nervous system (ANS) test results" as used in the specification and claims herein, shall be understood to include the Expiratory/Inspiratory (E/I) ratio, Standard Deviation (SD), Mean Circular Resultant (MCR), Coefficient of Variation, Valsalva Index, Posture Index, and/or any future invented calculation or combination thereof.

The E/I Ratio consists of calculating the time between successive heart beats during a predetermined breathing regimen consisting of paced breathing cycles of inspirations and expirations. Each breathing cycle is comprised of one inspiratory period and one expiratory period for a predetermined length of time. The calculation continues by identifying the maximum interbeat time during the expiratory period in the cycle, the minimum interbeat time during the inspiratory period in the breathing cycle, and then correlating these times using an established formula to produce the E/I Ratio. This formula consists of summing the maximum interbeat times of all expiratory periods and dividing that total by the sum of the minimum interbeat times of all inspiratory periods. To increase the accuracy of the E/I Ratio, the invention has the capability of further analyzing the morphology of each heartbeat to distinguish normal from abnormal beats. Abnormal beats, whether generated from the heart of the patient or any other source, cannot be "regulated" by paced breathing cycles. Thus, the capability to detect these abnormal beats and eliminate them from analyses will greatly increase the accuracy of the E/I Ratio.

It shall be understood that the term, "interbeat time", as used in the specifications and claims herein, is used interchangeably with the terms, "R—R interval", "peak-to-peak interval", heart beat interval" and/or "distance between selected point on one signal to the corresponding point on the succeeding signal".

The Standard Deviation is determined by measuring and recording all of the interbeat times during a predetermined breathing regimen such as twenty-five paced breathing cycles. Each breathing cycle consists of one inspiration and one expiration for a predetermined length of time. The mean interbeat time of the predetermined breathing regimen is calculated. All interbeat times are plotted in relation to this mean interbeat time to provide a statistical estimate, referred to as the standard deviation, of the variability of heart rate during the predetermined breathing regimen. Since the Standard Deviation is linked to the number of observations (i.e. heart rate), gradual changes in heart rate resulting from poorly paced breathing regimens, or accumulation of non-valid interbeat times due to the inability to identify abnormal beats, will erroneously influence the calculation of the Standard Deviation. Therefore, it is advantageous to have the capability to accurately pace the breathing and to distinguish between normal and abnormal beats to increase the accuracy of the ANS tests. This invention has the capability to increase the accuracy by incorporating its abnormal beat detection algorithms and providing its automated audiovisual instructions to the patient.

The Coefficient of Variation result is a derivative of the Standard Deviation computation described above, wherein the Standard Deviation value is divided by the mean interbeat time calculated during the predetermined breathing regimen.

To compute the Mean Circular Resultant (MCR), the invention identifies the time of each heart beat, as represented by an EKG signal, relative to the time of the beginning of each breathing cycle which is comprised of one inspiration and one expiration. An angular displacement (0–360 degrees) from the beginning of the breath cycle is calculated for each cycle. These angles are converted to vectors comprised of X and Y components for all breath cycles comprising the predetermined breathing regimen. The average X and Y components of these vectors are computed to form an "average vector". The MCR is the length of this vector. Any correlation between breathing and the number of heart beats will show up as a length that differs from zero. A perfectly random distribution of heart beats will generate a mean circular resultant at or close to zero. Although the MCR is tolerant of abnormal beats, this invention has the capability to continually differentiate normal from abnormal beats which will increase the accuracy of the other autonomic tests being simultaneously performed.

The Valsalva Index consists of calculating the time between successive heart beats and then relating the maximum interval during the predetermined breathing regimen to the minimum interval during a period of time following the predetermined breathing regimen. At the present time, the standard predetermined breathing regimen for performing the Valsalva test, also referred to a Valsalva maneuver, consists of a twenty-second period of forced expiration followed by a one minute "rest" period during which the patient breathes at his usual pace. To increase the accuracy, the invention has the capability to repeat the predetermined breathing regimens and to incorporate its abnormal beat detection algorithms during this ANS test.

The Posture Index is derived from calculating R—R intervals during the last portion of a series of positional changes by the patient. A predetermined regimen of posture changes are used to derive this Posture Index. At the present time, the standard positional changes consist of instructing the patient via the display means to stand for ten seconds, lie down for three minutes, and then stand for one minute. It is during the last minute of standing in which the maximum interbeat interval between the 25th and 35th beats is divided by the minimum interbeat interval between the 11th and 19th beats. The Posture Index, also referred to as the 30/15 Ratio, is then computed. This 30/15 Ratio was defined by Ewing in the references cited herein. For this calculation, the predetermined breathing regimen is the patient's usual non-paced rate of inspirations and expirations. This invention increases its accuracy with respect to the prior art due to the incorporation of its abnormal beat detection algorithms and its automated audiovisual instructions to the patient.

The term "predetermined physical regimen" shall be understood to include either the predetermined breathing regimen or the posture regimen defined above on which several other tests are based, and any other such future invented test adopted to be performed with the use of the invention.

It shall be understood that the term, "predetermined breathing regimen" and/or "predetermined posture regimen" and the like, as used in the specification and claims herein when describing the specific method for each ANS test, is performed according to established methods in practice today. However, it is conceivable that the predetermined breathing and/or posture regimens may change but the present invention would still be capable of working.

The audio-visual cues emitted by the present invention are unique because they instruct the patient in performing the predetermined breathing and/or posture regimens which are critical for the accurate assessment of autonomic nervous system function. Unlike the Cox '144 patent, the instructions of this present invention pertain to performing the test, whereas the Cox '144 instructional capabilities pertain to issuing of treatment modalities based on the analyses performed during the monitoring and recording of the EKG signal.

The external data handling and editing capabilities are new to this invention. The term, "external data handling means", as used in the specifications and claims herein, shall be understood to include all such optical emitters, receivers, and couplers used to transfer data to and from the apparatus to separate and/or remote data receiving devices. The external data handling means described herein is considered state-of-the-art, but it is conceivable that the handling means will change and the invention will still work. With the inclusion of the external data handling means, the capabilities of the Cox '144 patent are expanded to provide editing of the recorded, analyzed, and stored data. Any and/or all portions of the raw data can be reviewed, so that the data automatically selected by the invention by which it based its ANS test results, can be reselected, or edited. The ANS test results can then be recalculated based on the manually reselected data by the operator.

There is also a group of devices which are capable of monitoring and recording EKG signals either on magnetic tape (see U.S. Pat. No. 3,267,934 to Thornton) or in solid-state memory (see U.S. Pat. No. 4,679,144 to Cox et al), but neither of these devices are capable of correlating specific EKG intervals with specific respiratory and/or posture regimens.

The present invention relates to an instrument which non-invasively monitors EKG information in relationship to the respiratory cycle and/or postural changes, and more specifically it relates to a programmable self-contained instrument with automated audiovisual instructions to assist the patient and medical personnel in performing a series of ANS tests using predetermined breathing and/or posture regimens. The computations during these predetermined breathing regimens consisting of cycles of inspiration and expiration are automatically calculated, and provide a key index of measurement in determining the existence of underlying autonomic neuropathy which portends not only cardiac-related diabetic complications including myocardial infarction, but also other autonomic neuropathies effecting digestion, sexual function, pain perception, kidney function, eye sight, etc. Most recently, the detection of autonomic neuropathy, as determined by measuring beat to beat changes in heart rate (R—R intervals) has been shown to be useful in identifying patients at risk for sudden death and/or sleep apnea. The instantaneous ANS test results derived from this automated invention will be used by the physician to assess and manage his/her patients, such as diabetics with autonomic neuropathies and/or patients diagnosed with, but not limited to, coronary artery disease, or to assist the physician in the diagnosis of autonomic neuropathy resulting from undiagnosed underlying disorders such as diabetes or any other autonomic dysfunction or cardiovascular autonomic dysfunction which predisposes a patient to sudden death. It can also be used by the patient alone, with no assistance, when the patient is interested in self-monitoring the progression, or lack of progression, of autonomic neuropathy. Furthermore, any or all of the data used to compute the ANS test results can be reviewed and edited, if necessary, due to the invention's external data handling means. If the data that were automatically selected by the invention to compute its ANS results were invalid, the operator of the apparatus can reselect and manually input different data for automatic recomputation of the ANS test results.

DISCUSSION OF DIABETES

Diabetes mellitus is a chronic disorder characterized by abnormalities in the metabolism of carbohydrates, proteins and fats. There are approximately ten million diagnosed diabetics in the United States of America. Ten percent of known diabetics have Type I diabetes mellitus resulting in immunological destruction of pancreatic cells known as beta cells which are responsible for releasing insulin. Without these beta cells, the Type I diabetic does not produce sufficient insulin and therefore must take daily injections of insulin. The other ninety percent are Type II diabetics or non-insulin dependent. These patients are usually diagnosed after the age of thirty; however, the onset of Type II diabetes is insiduous and may go undetected and untreated for many years. Once diagnosed, these patients are often not dependent on insulin for survival but may be treated with either insulin or an oral hypoglycemic agent in conjunction with a proper diet and exercise regimen. The etiology of Type II diabetes mellitus remains unknown, although a number of genetic and environmental factors appear responsible.

In addition to those patients described above, another group of individuals have been described as having Impaired Glucose Tolerance (IGT), a borderline diabetic state. It has been shown that 25% of these invidulas with IGT eventually develop diabetes mellitus. In total, there are approximately fifty million people in the United States alone who have a form of diabetes mellitus or other glucose intolerances. Early detection of diabetes mellitus, regardless of its etiology (Type I, Type II, or IGT), is the best means for preventing and/or controlling diabetic complications which primarily result from years of untreated or poorly treated diabetes. Thus, early detection leads to early treatment, and the subsequent prevention of complications.

The diabetic is susceptible to a series of complications including both peripheral and autonomic neuropathies which result in morbidity and premature mortality. The morbidity and mortality of patients with diabetes mellitus is usually related to the macrovascular and microvascular complications of the disease which include retinopathy (retinal disease), nephropathy (kidney disease), amputations secondary to peripheral vascular disease (loss of toes), and myocardial infarctions secondary to coronary artery disease. Myocardial infarction is the leading cause of death in diabetics with onset after the age of thirty with the majority of these myocardial infarctions being silent. The absence of pain during a myocardial infarction in the diabetic patient has been attributed to autonomic neuropathy.

About 50 percent (or more than 35,000) of nontraumatic leg and foot amputations in the U.S. are the result of diabetes. Each year 5,000 diabetics lose their sight. Ten percent of all diabetics develop nephropathy, accounting for thirty percent of new cases of renal disease in the U.S. each year. These diabetic complications, which include both peripheral and autonomic neuropathies, occur in some form in every diabetic and usually occur in concert with each other. Experimental evidence suggests that diabetic neuropathy is the result of an abnormal accumulation in the nerve fibers of chemical substances called polyols, which produce segmental demyelination (loss of segments of the nerve covering), a process that results primarily from hyperglycemia, or excess glucose.

Clinical peripheral neuropathy is characterized by symptoms of sensory loss, paresthesias (abnormal skin sensations), gross and fine motor incoordination, and pain, and is thus usually perceived by the patient. Peripheral neuropathy is often assessed by asking the patient to describe his symptoms but may also be assessed by nerve conduction tests. Symptoms of autonomic neuropathy, on the other hand, may be more insidious in onset and therefore less obvious to the diabetic. For example, bladder dysfunction, postural hypotension, gastric distention, sweating aberrations, and pupillary abnormalities may not even be noticed or may be ignored by the patient. Despite the "silence" of autonomic neuropathies, they carry a greater morbidity than peripheral neuropathies.

The problem facing medical practitioners is that visual symptoms of these complications are not revealed until a fairly advanced stage has been reached. Furthermore, the diagnostic tests available for assessing peripheral and autonomic function are either 1) invasive, 2) labor intensive, 3) insensitive, 4) difficult to interpret, 5) cumbersome, and/or 6) expensive. As a result, despite the awareness of these autonomic neuropathies resulting from diabetes and other causes, and potentially affecting 50 million people in the U.S. alone, these complications remain undiagnosed and/or unmanaged for many years.

Although the above discussion focused on diabetes and its damaging effects on the autonomic nervous system, there are a number of other conditions which adversely affect the functioning of the autonomic nervous system including alcoholism, Parkinsonism, sleep apnea, impotence, toxic reactions, connective tissue diseases such as multiple sclerosis or Shy-Drager Syndrome, and most recently discovered, the human immunodeficiency virus (HIV). The association of autonomic neuropathy and these conditions has been described in the following articles: "Autonomic Neuropathy in an Alcoholic Population, Postgraduate Medical Journal 1987, 63:1033–1036; "Systemic Sclerosis: Another Disease with Autonomic Dysfunction 1988, American Neurological Association, 421–422; "Somatic and Autonomic Function in Progressive Autonomic Failure and Multiple System Atrophy 1987, American Neurological Association, 692–699; "Disorders of the Autonomic Nervous System; Part 1. Pathophysiology and Clinical Features 1987, Annals of Neurology, 21; 5:419–426; "Autonomic Neuropathy in AIDS", Lancet, 1987, Aug. 8:343–344; "Autonomic Neuropathy and HIV Infection", Lancet, 1987, Oct. 17:915. The value of assessing heart rate variability as a means to identify patients at risk for sudden death has been described in these articles: Kleiger R. E., Miller J. P. et al. "Decreased Heart Rate Variability and Its Association with Increased Mortality After Acute Myocardial Infarction", American Journal of Cardiology, 1987; 59: 256–262; Martin G. J., Magid N. M. et al. "Heart Rate Variability and Sudden Death Secondary to Coronary Artery Disease During Ambulatory Electrocardiographic Monitoring", American Journal of Cardiology, 1987; 60: 86–89; Bigger J. T. Kleiger R. E. et al. "Components of Heart Rate Variability Measured During Healing of Acute Myocardial Infarction", American Journal of Cardiology, 1988; 61: 208–215; Rothschild M., Rothschild A., and Pfeifer M. "Temporary Decrease in Cardiac Parasympathetic Tone After Acute Myocardial Infarction", American Journal of Cardiology, 1988;62: 627-639.

Despite the increasing body of literature regarding autonomic neuropathy resulting from conditions other than diabetes, most of the information to date pertaining to the assessment and diagnosis of autonomic nervous system function by means of evaluating heart rate, or R-R, variability during predetermined breathing and/or posture regimens has been derived from the diabetic population. However, there have been several recent studies which have focused on the value of assessing heart rate variability in patients with or without diabetes as a means to detect patients at risk for sudden death due to changes in autonomic tone. Such detection will then be used for appropriate stratification of patients to additional diagnostic tests and/or therapeutic maneuvers. Thus, the range of values for the E/I Ratio, Standard Deviation, Mean Circular Resultant, Valsalva Index Posture Index and Coeffiecient of Variation, which are indicative of an abnormal or borderline functioning of the autonomic nervous system, has been based on extensive studies of diabetic patients. However, the range of values may change depending upon the results of ongoing research, but the present invention would still be capable of working. Therefore, until definitive studies are completed for each specific subset of patients being evaluated by the present invention, the values incorporated into the present invention may be used to diagnose autonomic dysfunction resulting from any condition. "Normal" values have been derived from patients with no known disease states.

DISCUSSION OF THE PRIOR ART

Concern for patients with peripheral and autonomic neuropathy has led to the development of some devices for the assessment and diagnosis of these conditions. However, these prior art devices have the limiting factors previously discussed; these limitations are not present in this invention.

As for peripheral neuropathy testing, there are a number of nerve conduction tests currently in use today. These tests are performed by applying a small shock to the nerves, for example, between the knee and the ankle. The voltage is then recorded with electronic amplifiers from a disk pasted to the skin overlying the individual muscle being tested. In neuropathy, the speed of the impulse along the nerve is decreased, indicating an abnormality. This test is labor intensive and is only capable of evaluating one portion of a peripheral nerve at a time. The results are not indicative of generalized peripheral neuropathy or autonomic neuropathy.

Another type of peripheral neuropathy test is needle electromyography whereby a needle is inserted into several muscles and the electrical discharges are recorded. While this test may evaluate peripheral nerves, it is invasive, expensive, and often not tolerated by the patient because it is extremely painful.

These are the only currently available methods of objectively evaluating peripheral neuropathy. Typically, and most frequently, peripheral neuropathy is evaluated by a physician during a physical exam whereby the physician will test one's reflexes and one's ability to feel different kinds of sensations at various places on the skin using a reflex hammer and pointed object such as a pin. The results are based on the patient's perception of pain, and the physician's quantitative assessment of the patient's reflex movements. Since these tests are not quantitative, it is therefore difficult to accurately evaluate the progression, or lack of progression, of peripheral neuropathy from one office visit to the next.

Furthermore, these tests are not applicable to autonomic nerve testing since autonomic function is neither isolated to a specific nerve nor are the affected nerves or organs located in accessible areas. The autonomic nervous system, also known as the involuntary nervous system, provides innervation to the heart, blood vessels, glands, and other visceral organs and smooth muscles. Hence, the autonomic nervous system is widely distributed throughout the body.

For autonomic neuropathy testing, which consists of evaluating both sympathetic and parasympathetic activity, one of the easiest organs to test for autonomic dysfunction is the heart. The measurement of heart rate variation (R-R testing) during paced cycles of respiration has been well documented as a means to specifically assess the parasympathetic branch of the autonomic nervous system. One system for evaluating heart rate variability has been described by Rothschild et al in a paper published in Diabetes Care, Vol. 10, No. 6, November-December 1987 entitled "Sensitivity of R-R Variation and Valsalva Ratio in Assessment of Cardiovascular Diabetic Autonomic Neuropathy". This system consisted of several separate components including an oscilloscope, EKG machine, and a stop watch. The patients had to be instructed by a trained individual during the entire test on the proper breathing regimens to be performed. Analysis of the results were then performed retrospectively on a computer with intervention by a skilled individual. Another system for recording, analyzing, and correlating R-R interval with respiration is described in Diabetes Care, Vol. 7, No. 5, September-October 1984 entitled "R-R Interval Studies: A Simple Office Protocol for Evaluation of Cardiac Autonomic Neuropathy". This system also consisted of several components including an EKG machine and a stopwatch. As described, a series of manual steps had to be performed and synchronized at specific times during the respiratory cycles. These particular configurations of equipment for R-R testing require multiple components and skilled individuals for instructing the patient and analyzing the results, thus producing costly, labor-intensive, and cumbersome systems.

Furthermore, in order to obtain accurate results, the test methodology must be precise; that is, respiratory cycles must be paced regularly and the R-R intervals must be precisely correlated with the respiratory cycles so that the analyses reflect an accurate assessment of the autonomic nervous system. Additionally, it is critically important to distinguish between normal and abnormal beats because abnormal beats occur at irregular intervals and can not be "regulated" by paced respiration. Thus, inaccurate detection of beats can greatly skew the results with the exception of Mean Circular Resultant which is a computation that is tolerant of abnormal beats included in the analysis. Consequently, the beat detection capabilities described in the Cox '144 patent are advantageous for increasing the accuracy when calculating the E/I, Standard Deviation, Coefficient of Varation, Valsalva Ratio, and Posture Indices.

The accuracy of the above described prior art is further compromised when an individual attempts to manually conduct these tests because of the simultaneous tasks which must be performed including instructing the patient on precise breathing and/or posture regimens while looking at a stopwatch, recording the EKG manually, and counting the number of required respiratory cycles and/or postural changes.

To evaluate the sympathetic branch of the autonomic nervous system, the Valsalva maneuver has proven to be a useful method. A system to perform the Valsalva maneuver has also been described by Rothschild in the article previously cited. This system also consists of several components as well as retrospective analysis of the results and the lack of automated instructions.

More specifically, to perform the Valsalva test, which includes forced expiration against against a resistance, the patient is instructed by a technician or physician to blow through the mouthpiece attached to a manometer so that the forced exhalation is sustained for twenty seconds at a pressure of 40 mm of mercury. The patient is then instructed to breathe normally for one minute before repeating the above described Valsalva maneuver. During each phase of the maneuver, forced exhalation followed by relaxed breathing, the patient is continually monitored with an EKG machine. One system for evaluating heart rate variability during the Valsalva maneuver is described by Rothschild cited above. This system consisted of recording the EKG signal onto magnetic tape for further off-line analysis by a computer. The heart rate variation was determined by a vector-analysis technique to calculate the maximal heart rate interval, expressed as milliseconds, divided by the minimal heart rate interval. The present invention provides for an automated method for performing the Valsalva test. With the use of audiovisual cues, the apparatus instructs the patient on the predetermined breathing regimens recommended for the Valsalva test while being monitored electrocardiographically by a sensing means attached to the patient and connected to the apparatus. The sensing means consists of the state-of-the-art electrodes disclosed in U.S. Pat. No. '144 but it is conceivable in the future that sensing means will change and the invention will work. Thus, the term, "sensing means", as used in the specification and claims herein shall be understood to include all such electrodes, ultrasound and the like devices. This ANS test result, referred to as the Valsalva Index, is computed by calculating the time between successive normal beats only, and then relating the maximum heart rate interval during the forced expiratory period of the predetermined breathing regimen to the minimum heart beat interval during the period of time of relaxed breathing following the forced expiratory period. The test result is instantaneous and automatic.

An additional test performed by a system described by Ewing in an article previously cited to evaluate the parasympathetic branch of the autonomic nervous system is the posture test. To perform this test, the patient lies quietly on a couch and is then instructed by a technician to stand up for a minimum of thirty heart beats. Throughout the test, the patient is monitored electrocardiographically. The Posture Index is derived retrospectively either by manually measuring R-R intervals or by analyzing the ECG data on an off-line computer. The present invention provides for an automated method and apparatus for performing the posture test. With the use of audiovisual cues, the invention apparatus instructs the patient on the predetermined posture regimens recommended for the posture test while being monitored electrocardiographically by a sensing means attached to the patient and connected to the apparatus. The derived ANS test result, referred to as the Posture Index, and/or 30/15 Ratio, is automatically and instantaneously calculated upon conclusion of the posture test by the invention device.

SUMMARY OF THE INVENTION

In summary, starting from this posture technology, the invention goes forward to provide a portable, automated, programmable, self-contained heart monitoring device which in real-time on-going manner "looks at" each and every heart beat as it relates to specific predetermined breathing and/or posture regimens. It further instructs the patient during each ANS test as to the proper breathing and/or posture regimen to be performed using automated audiovisual cues. Because of the data analysis and storage abilities and the speed and configuration of current computer technology which are used in the invention, the invention gives the patient the benefit of undergoing several tests simultaneously for assessing autonomic nervous system functioning which would usually not be offered due to the inherent difficulties and expense with the currently available systems. Thus, the invention is a dramatic step forward in performing automated autonomic nervous system testing using predetermined paced breathing and/or posture regimens, and instantaneously computing, disclosing, and editing the ANS test results. Thus, the early diagnosis and management of autonomic nervous system dysfunction resulting from diabetes and other diseases is facilitated by the automated test methods of this invention.

Further, the method and apparatus of the invention provide a gamut of tests so that both the sympathetic and parasympathetic branches of the autonomic nervous system can be evaluated, provide the ability to calculate heart rate variation by detecting any major peak of the QRS complex, not just the R-wave; provide the ability to discriminate between normal and abnormal beats which will increase the accuracy of the tests; provide the ability to program the monitor to perform one or all of the autonomic nervous system tests; provide the capability to immediately review the test results for verification of the apparatus' selection of data used for calculation of the ANS test results; and provide the capability to manually select other data for immediate recalculation of the ANS test result.

The above and other advantages of the invention will become clear from the following detailed description when read in conjunction with the accompanying drawings also forming part of this disclosure in which:

BRIEF DESCRIPTION OF THE DRAWINGS

FIG. 4 is a schematic of the logic that controls the performance of any of the autonomic nervous system tests.

FIGS. 6 and 7 show the system logic for analyzing and categorizing the type of abnormal beats that are judged to be representative of EKG signals generated from the heart of the patient.

DETAILED DESCRIPTION OF THE PREFERRED EMBODIMENTS

Figure 1:
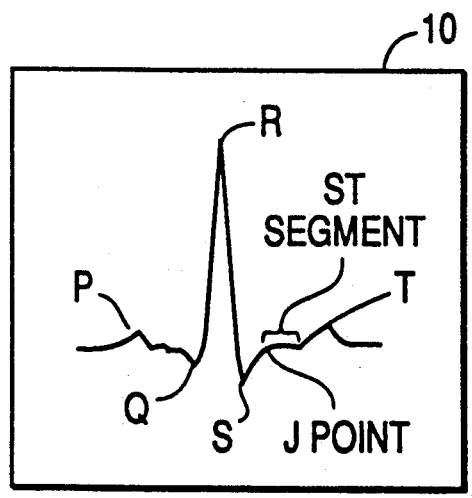
FIG. 1 shows an EKG trace for a heart beat from a healthy person and the conventional names of the parts of the waveform.

Referring now to the drawings in more detail, FIG. 1 depicts a typical ECG waveform of the heart of a normal, healthy person which includes two heart beats, each of which includes a P wave of positive polarity, a QRS complex consisting of a negative Q wave, a positive R wave, a negative S wave, and finally a T wave separated from the QRS complex by an ST segment. J is a point in the ST segment and defines the end of the S portion thereof.

Figure 1A:
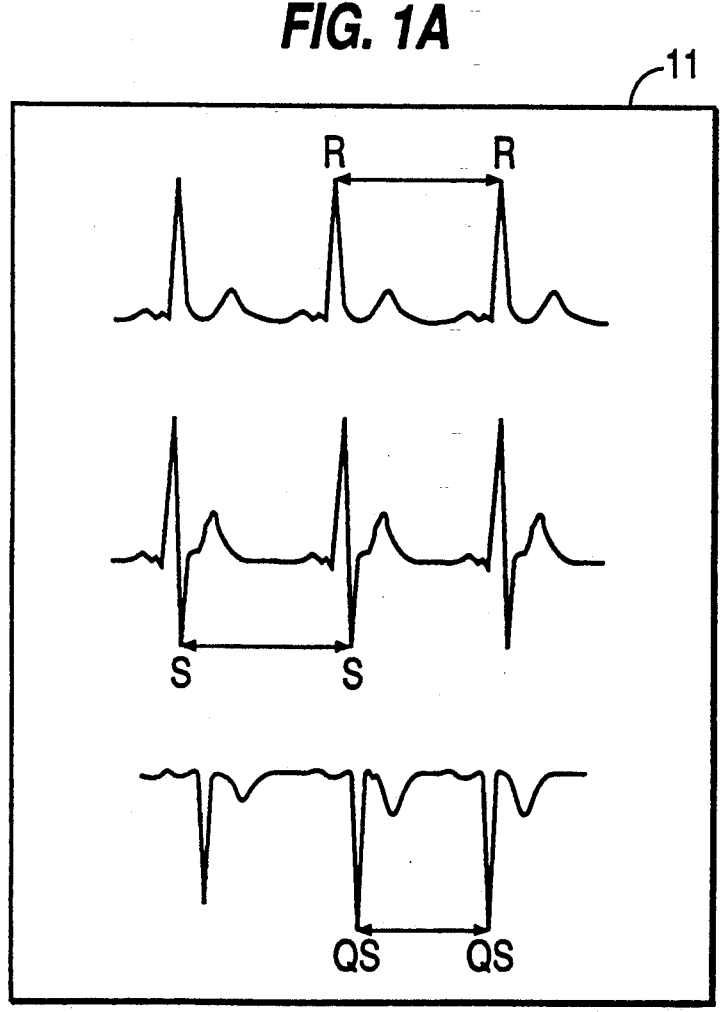
FIG. 1a shows two other EKG traces which could be taken from different unhealthy persons, or which may occur in healthy persons depending upon the placement of the sensing means on the chest.

FIG. 1A illustrates other ECG waveforms which differ from the "typical" ECG complex. These morphologies may result from underlying pathology of the myocardium (heart muscle) or from monitoring the heart from different areas on the chest. As shown, not all ECG waveforms may consist of P-Q-R-S-T waves. Therefore, other intervals besides R-R may be used to calculate distances between successive beats. These intervals may include QS-QS, S-S, etc . . . as shown in FIG. 1A.

Normally, in a healthy person with an intact autonomic nervous system, the EKG signals will fluctuate with the respiratory cycle. Specifically, the heart rate will increase during inspiration and decrease during expiration. In other words, the R-R distances are measured, and these distances are then expressed as milliseconds or beats per minute, or more commonly referred to as heart rate. Measurements can also be made between Q-Q, QS-QS, or any other corresponding points on succeeding EKG signals. In normal subjects, these heart beat intervals are shortened during inspiration and prolonged during expiration. In people whose autonomic nervous system has been damaged or is dysfunctional, these heart beat intervals remain constant or nearly constant throughout both phases of the respiratory cycle—inspiration and expiration. This fact, the failure of these intervals to respond normally in response to respiration has been documented as a clinical manifestation of underlying autonomic nervous system dysfunction resulting from a number of systemic diseases such as diabetes mellitus, parkinsonism, chronic kidney failure, alcoholism, toxic or pharmacologic agents, or numerous neuropathic diseases. Heart rate variation in response to respiration is well recognized as reported by Wheeler and Watkins in the British Medical Journal, 1973, in a paper entitled, "Cardiac Denervation in Diabetes". Heart rate variation is particularly pronounced during deep breathing at a frequency of six breaths per minute. Conversely, heart rate variation is greatly diminished or absent in people such as diabetics who have had damage to their vagus nerve which intrinsically controls heart rate in response to stimuli such as breathing.

Figure 2:
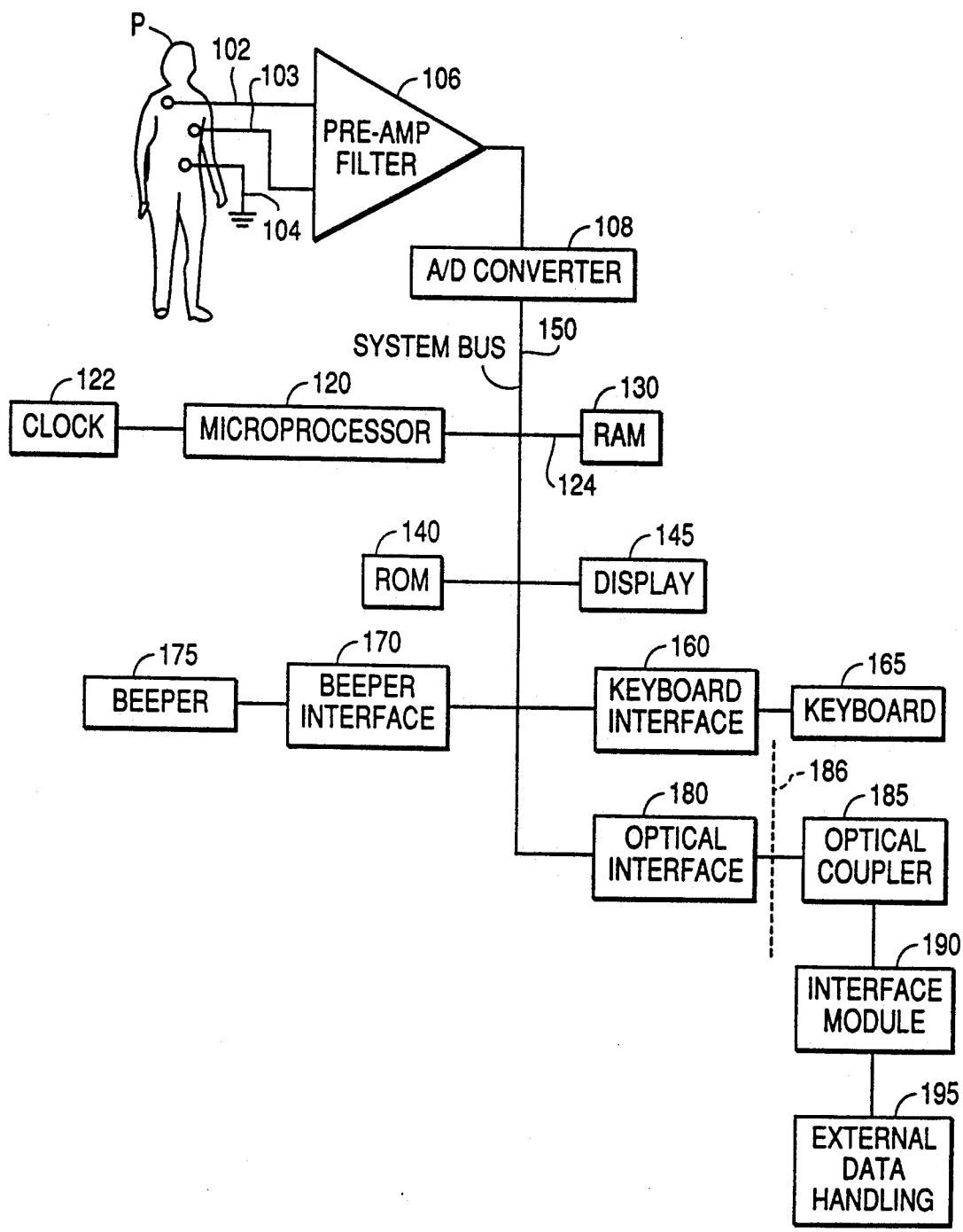
FIG. 2 is an overall block diagram of the hardware components comprising the apparatus of the invention.

Referring now to FIG. 2, this diagram is being incorporated in its entirety with an additional external data handling means by reference to U.S. Pat. No. 4,679,144 to Cox et al wherein the present invention is co-owned by the inventors of the aforementioned patented invention.

In FIG. 2, "there is shown a generalized schematic view of the apparatus of the present invention in which leads 102, 103, and 104 represent electrodes and wires attached to the patient P at predetermined locations preferably in a conventional manner (the preferred embodiment envisions non-intrusive electrode-to-patient sensing means). The sensing means are preferably of the type of electrodes disclosed in U.S. Pat. Nos. 3,420,223, 3,490,440, and 3,665,064. Lead 104 functions to ground the apparatus, while leads 102 and 103 feed EKG signals, detected by the electrodes, to a pre-amplifier and filtering component 106 to perform two functions: First, to amplify the signals detected by the electrodes, and second to eliminate undesirable noise. The amplifier, while of conventional design, must provide a uniform bandwidth to effectively amplify all of the components in the EKG signal without producing any distortions so that the output signal from the amplifier is a true and amplified reproduction of the EKG signal picked up by the electrodes".

"The output of the amplifier is fed to a converter 108 of the analog-to-digital (A/D) type. The converter is connected, via a system bus 150, to a microprocessor 120 driven by a clock 122 through connection 124, one or more random access memory (RAM) components 130, one or more read only memory (ROM) components 140, an alpha-numeric display device 145, a keyboard 165, an alarm means 175, and an optical emitter 185 with an optical interface to couple emitter 185 to system bus 150. A lithium battery (not shown) can be employed as a back-up for the memory components. A keyboard interface component 160 couples keyboard 165 to the system bus 150, and an interface 170 couples alarm means 175 to the system bus 150." The alarm means 175 may consist of a beeper or other alarm means. The output from the optical interface 180 is sent to an optical coupler 185 which is not situated on the apparatus as indicated by the dotted line 186. Information can be either received from or emitted to the interface module 190 via the optical coupler 185. The information is then stored in the interface module 190 for immediate or future output to an external data handling means 195 which may consist of a modem, printer, or computer, or other external data handling means. The speeds, capacities, etc. of the hardware components needed to implement the invention can be determined by persons skilled in these arts, based on the teachings herein.

Figure 3:
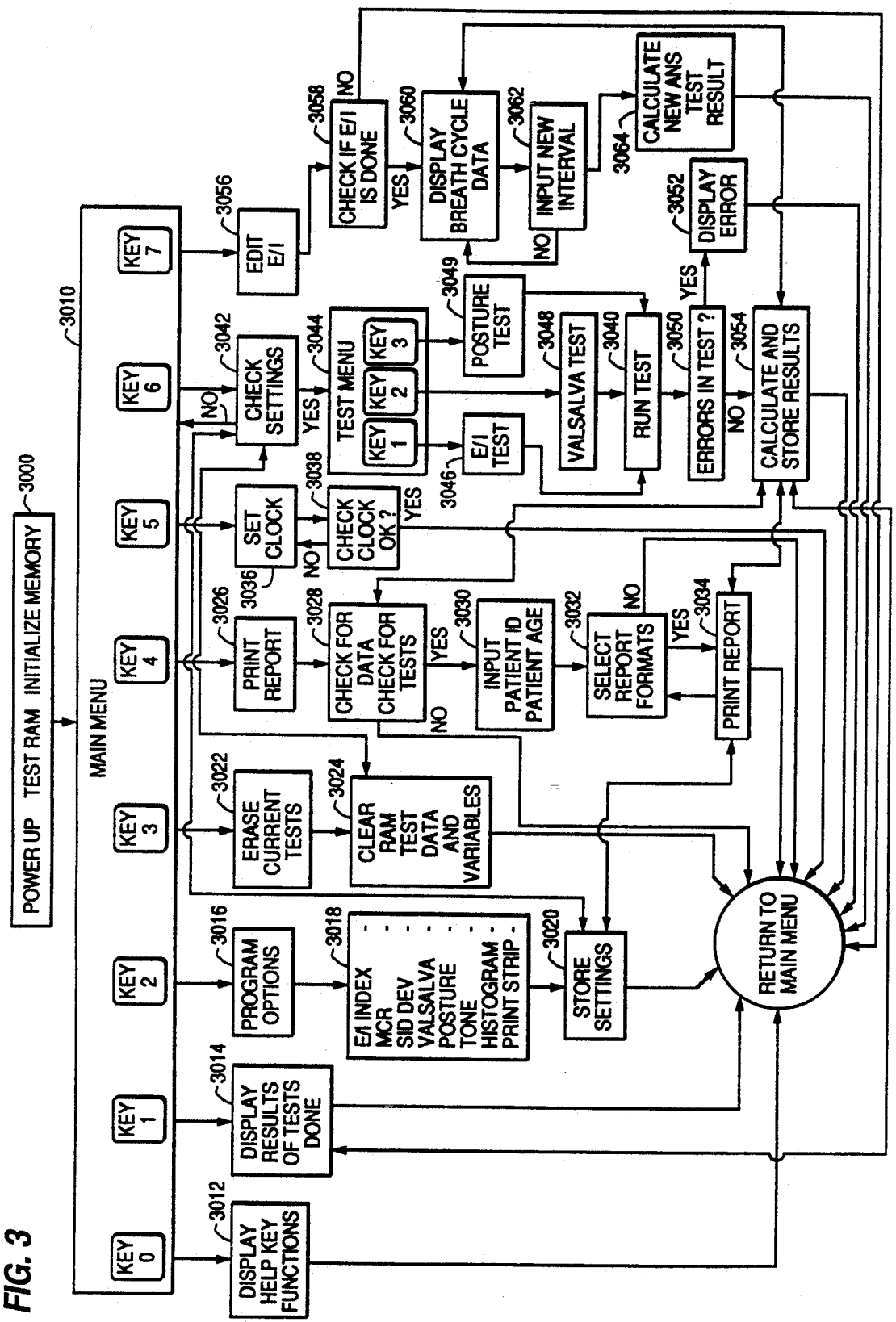
FIG. 3 is an overall block diagram depicting the software logic controlling the different functions of the invention.

Referring to FIG. 3, there is shown a generalized schematic view of the program flow. When the invention is turned on, Block 3000 powers up the microprocessor which in turn performs a series of checks to make certain that the invention is functioning properly. This series of checks includes initializing all hardware elements to the proper configuration for system operation and testing the Random Access Memory (RAM) to insure that data can be stored and retrieved properly. When the system is ready, a Main Menu 3010 is displayed which provides a starting point from which the operator may access a desired function. If the operator is not familiar with the direct access keys to each of the different functions, Key "0" provides a HELP menu 3012 which lists the functions and their corresponding access keys.

If Program Options 3016 is selected from the Main Menu, the program advances to Block 3018 whereby operator is prompted to select 1) one or all of the autonomic nervous system tests to be performed, 2) the format of the printed test results, and 3) the audible alarm setting that assists the patient in pacing the respiratory cycles during the paced breathing regimens. If the TONE is programmed "ON", a tone will rise in pitch for inhalation and fall in pitch for exhalation during the performing of any predetermined breathing regimen as a means to pace the person's breathing regimens. The display 145 also paces the person's breathing regimens by means of a moving bar which lengthens for inhalation and decreases in length for exhalation. As a selection is made for an option, the program advances to the next option until all selections have been made. If no selection has been made, the display will read "NO OPTION SET", and the program will remain at Block 3018 until at least one selection is made. The selections are then stored in Block 3020, and the program logic returns to the Main Menu 3010. Once the program options have been selected, the operator selects the clock function by pressing Key 5 on the Main Menu 3010. The clock function is accessed, and the time and date are displayed for review. To set the correct time and date in Block 3036, the operator presses the appropriate keys on the keyboard 165. Once the clock is set, the Real Time Clock 122 is checked 3038. If the clock has not been set, the program returns to Set Clock 3036 and prompts the operator to reset the clock. Once the clock is set and the program verifies that a valid time and data have been entered, the program returns to the Main Menu 3010.

Prior to performing an autonomic nervous system test, the operator erases any current tests stored in RAM by accessing the Erase option 3022 with Key 3 on the Main Menu. The program checks to see if there are stored test data and variables in Block 3024 and proceeds to clear the Random Access Memory (RAM) if prompted by the operator to do so by pressing a verification key on the keyboard. The program returns to the Main Menu 3010.

When Key 6 is selected from the Main Menu 3010, the RUN TEST procedure is accessed, and the program advances to Check Settings 3042 where two checks are made. The first check is made on autonomic nervous system (ANS) test program settings in Block 3020. At least one ANS test resulting in one of the following test results—E/I Index, Mean Circular Resultant, Standard Deviation, Valsalva, or Posture, must have been chosen. If no tests have been chosen, the display 145 is changed to read "NO OPTIONS SET" and the program returns to the Main Menu 3010. A second check is made to see if test data and variables have been erased. If they have not been erased, the program will prompt the operator with a message, "DATA NOT ERASED", and the program loops until any key is pressed. At key entry the program returns to the Main Menu 3010.

If at least one of the program options was selected in Block 3018, and if all current tests were erased in Block 3024, the program advances to the Test Menu 3044 which will display the programmed test options. The operator may choose to perform the ANS tests in any order by selecting the key corresponding to either the E/I test 3046, Valsalva 3048, or Posture 3049.

The E/I test 3046 will be considered first. Specifically, when the E/I test is selected, the program advances to Run Test 3040. Previously selected test options are checked and test parameters are set. A period of predetermined breathing regimens, lasting for at least one minute, follows in which the patient is able to practice the predetermined breathing regimen, guided by the display 145 and a tone 175 (if activated prior to the start of the actual test). The EKG signal is checked to insure sufficient quality for the test. The EKG signal checking logic, also referred to as beat detection, is described in detail in FIG. 5. After sixty seconds, the program prompts the patient to begin the test when convenient by means of a visual cue on the display 145.

The Valsalva test 3048 operates similarly. After selecting this option, the Run Test portion 3040 is accessed which initiates an EKG signal check and provides a practice period for the patient wherein the patient may practice the predetermined breathing regimen consisting of forced exhalation and non-paced breathing. If the EKG signal is acceptable, the program prompts the patient with a visual cue to begin the test by exhaling forcefully for twenty seconds at a metered rate. After the forced exhalation, there is a recovery period consisting of a sixty-second period of non-paced relaxed breathing during which time the patient's heart rate continues to be monitored electrocardigraphically. At the conclusion of the recovery period, the program provides an audiovisual cue to indicate the end of the test.

The Posture test 3049 is also similarly performed although the Run Test 3040 parameters include a predetermined posture regimen and a predetermined breathing regimen comprised of only non-paced relaxed breathing. Following a sixty-second period of EKG signal checking, the patient is prompted visually to stand for approximately ten seconds, lie down for three minutes, and then stand again for sixty seconds. The patient is prompted with an audiovisual cue when the test is completed.

At the completion of each ANS test, the program checks for any errors 3050 that may preclude the calculation of the ANS test result. Such errors include insufficient or excessive number of EKG signals detected during the running of any test. Since all ANS test results are based on R-R intervals occurring at specific times during the predetermined breathing regimens, the program verifies that the necessary R-R intervals have been obtained. If errors are present, the program prompts the person by displaying the error message such as "RATE TOO SLOW", "RATE TOO FAST", or "SIGNAL TOO WEAK" in Block 3052 before returning to the Main Menu upon any key hit. If no errors are present, the program advances to calculating and storing the ANS test results 3054 before returning to the Main Menu 3010. The calculations are described in more detail in FIGS. 8 and 9. The ANS test results are stored in RAM 130 until erased.

After the results are calculated and stored, the operator may transmit the ANS test results to an external data display means by pressing Key 2 on the Main Menu. When selected, the program checks for the storage of at least one ANS test result in Block 3054. If no results are stored, the program alerts the operator that "NO DATA" are stored and the program loops until any key is pressed. On key hit the program returns to the Main Menu 3010. If one of the ANS tests have been completed, the program displays the first selected ANS test result followed by the remaining test results. After all results have been displayed, the program returns to the Main Menu 3010. In addition to transmitting the ANS test results to an external data display means, the operator may choose to transmit the results to an external data handling means which may include a printer, a computer, or other data handling means. Transmitting ANS test results is also referred to as "printing" throughout the descriptions and flow charts that follow. This printing option 3026 may be accessed by pressing Key 4 on the Main Menu 3010.

Prior to transmitting the ANS test results to an external data handling means, Block 3028 first checks to see if any ANS results have been computed and stored in Block 3054. If no tests have been done, the program bypasses the other print options and returns to the Main Menu 3010. If a completed test(s) and result(s) are present, the program advances to Input 3030. The operator is prompted to enter the Patient ID and Patient Age. The input Patient Age is used to correlate the ANS test results with age-matched values. This automated correlation is unique to this invention and is critical for accurately assessing the extent of autonomic nervous system functioning because the E/I Ratio declines appreciably with age. Therefore, different value ranges are required to account for the normal aging process. The program advances to Report Format 3032 where the operator individualizes the report format, if so desired. If the Strip Printing Option is selected, a minimum of one minute of ECG data recorded during the predetermined breathing regimens will be printed. The actual amount of ECG recording to be printed is based on the next selection by the operator. A LONG report will consist of all ECG data recorded during the predetermined breathing regimens whereas a SHORT report will consist of only the initial minute, or first six breath cycles, of the paced breathing regimens. The "Print Grid" option will determine whether a grid will be printed behind the ECG data. Regardless of the selected format, each report will contain the following information: Heading, Patient ID number, Patient Age, Date, Software version, and Procedure Text. The Procedure Text describes which ANS tests were performed. Once all options have been selected, the operator is prompted to choose either to transmit the report, or to abandon the print task and return to the Main Menu. If the report is transmitted, the program advances to Print Report 3034. The printed report will output the ANS test results and their corresponding age-matched values in addition to the raw ECG data.

The printed report will also contain the following information based on the prior selections stored in Blocks 3020 and 3032. First, the Histogram option is checked in Block 3020. If it has not been selected, the program checks the Strip Option in block 3032. If the E/I test was selected and performed, a table is printed based on the data stored in Block 3054 which lists each breath cycle number in block 3054, the inhalation heart beat interval chosen for each breath cycle number and its duration in milliseconds, the exhalation heart beat interval number chosen for each breath cycle number and its duration in milliseconds, as well as the duration totals in milliseconds for both inhalation and exhalation periods comprising the breath cycles. This is followed by a histogram which graphs the heart beat intervals over the breathing regimens, referred to as "time". This is followed by a graph of the frequency distribution of the heart beat intervals over time. If the Valsalva test was completed the Valsalva histograms are also printed. One graph for each test is printed showing the heart beat intervals over time. Each graph is labeled with the corresponding Valsalva test number. The Strip option is checked lastly in block 3032. If this option was selected, the strips are printed and annotated with the following information: Inhale or Exhale, Breath Cycle Number, Interval number for those intervals used to compute the E/I Ratio and/or other ANS test result, and the interval selected in each breath cycle is printed in bold to highlight the automatic selection by the apparatus. In addition a page top heading lists the Patient ID, the page number and the date. At the conclusion of the strip printing the program returns to the Main Menu 3010.

The Editing option of the apparatus corresponds to Key 7 on the Main Menu 3010. As previously explained, the E/I Ratio is derived from selected heart beat intervals in each breath cycle which have been automatically selected by the apparatus upon completion of the predetermined breathing regimens comprising the ANS tests. The operator, however, has the option to manually reselect the heart beat intervals to be used for recomputing the E/I Ratio and/or any other ANS test result. Some or all of the intervals which had been automatically selected by the apparatus may be reselected and manually input into the apparatus for automatic recomputation.

Upon selection of the EDIT E/I option 3056, the program checks to insure that the E/I test was completed in block 3058. If no test was done the program returns to the Main Menu. If the test has been completed, the program displays breath cycle data in Block 3060 which is obtained from data storage Block 3054. The data is displayed on the external display means including the specific breath cycle (inspiratory or expiratory) of the predetermined breathing regimen the heart beat interval automatically selected by the apparatus for that breath cycle which was used in the ANS test result computation, and the start and end heart beat intervals of that same breath cycle. The operator may manually input a new heart beat interval 3062 from the keyboard as represented by a number from the range of numbers representing the heart beat intervals between start beat and end beat for that breath cycle as displayed in block 3060. A check is made for valid entry in block 3060. A tone is sounded to indicate a non-valid entry and the program returns to 3062. A valid selection allows the program to advance to the next breath cycle of the predetermined breathing regimen until all breath cycles have been reviewed. The E/I Ratio and/or other ANS test result using the reselected heart beat interval value is automatically recomputed in block 3064. The E/I Ratio and/or other ANS test result may be recomputed until the ANS test result is acceptable to the operator. The program returns to the Main Menu 3010 after each recomputation.

Referring now to FIG. 4, the RUN TEST Block 3040 from FIG. 3 is shown in more detail. This block is repetitively executed throughout the running of each ANS test. At the start of any autonomic nervous system test, the program advances to the audiovisual branch 3040-1 of RUN TEST 3040 which is responsible for issuing audiovisual messages on the external display means as to the detection of incoming signals and instructions to guide the patient in performing the predetermined physical regimen. Once signals are received, the program advances to Beat Detection 3040-2 to determine whether the signals are ECG signals generated from the heart of the patient or if they are artifactual. Beat Detection is described in more detail in FIG. 5. The program must then distinguish whether the Beat Detection is occurring during Setup 3040-3 wherein the patient may practice the predetermined breathing regimen before the start of the actual test run, or during the ANS test itself 3040-6. If the program is in the Setup phase, the program advances to Block 3040-4 to determine whether the Setup phase is completed. The Setup lasts for a minimum of one minute. If one minute has elapsed, and if the patient and/or technician depresses a button on the external apparatus signaling the onset of the actual test, the program advances to 3040-5 where a check is made on the ECG signal during the Setup phase to determine whether the ECG signals meet criteria as described in more detail in FIG. 5. If errors are present, the program returns to Block 3050 wherein additional error checking is completed. If, however, one minute has not elapsed, or the patient and/or technician has not depressed the start button when the program is at Block 3040-4, the program returns to Block 3040-1 where audiovisual instructions will continue to be displayed. When the program returns to Block 3040-3, and the predetermined breathing regimen is not in the Setup phase because an external signal has been received indicating the end of the Setup, the program branches to the actual test portion 3040-6 of the predetermined breathing regimen in Block 3040-6. When predetermined breathing regimen is completed in Block 3040-6, the program advances to Block 3050 which is described in detail in FIG. 3. If the predetermined breathing regimen has not been completed according to criteria previously described for each ANS test, the program returns to Block 3040-1 where audiovisual instructions continue.

Figure 5:
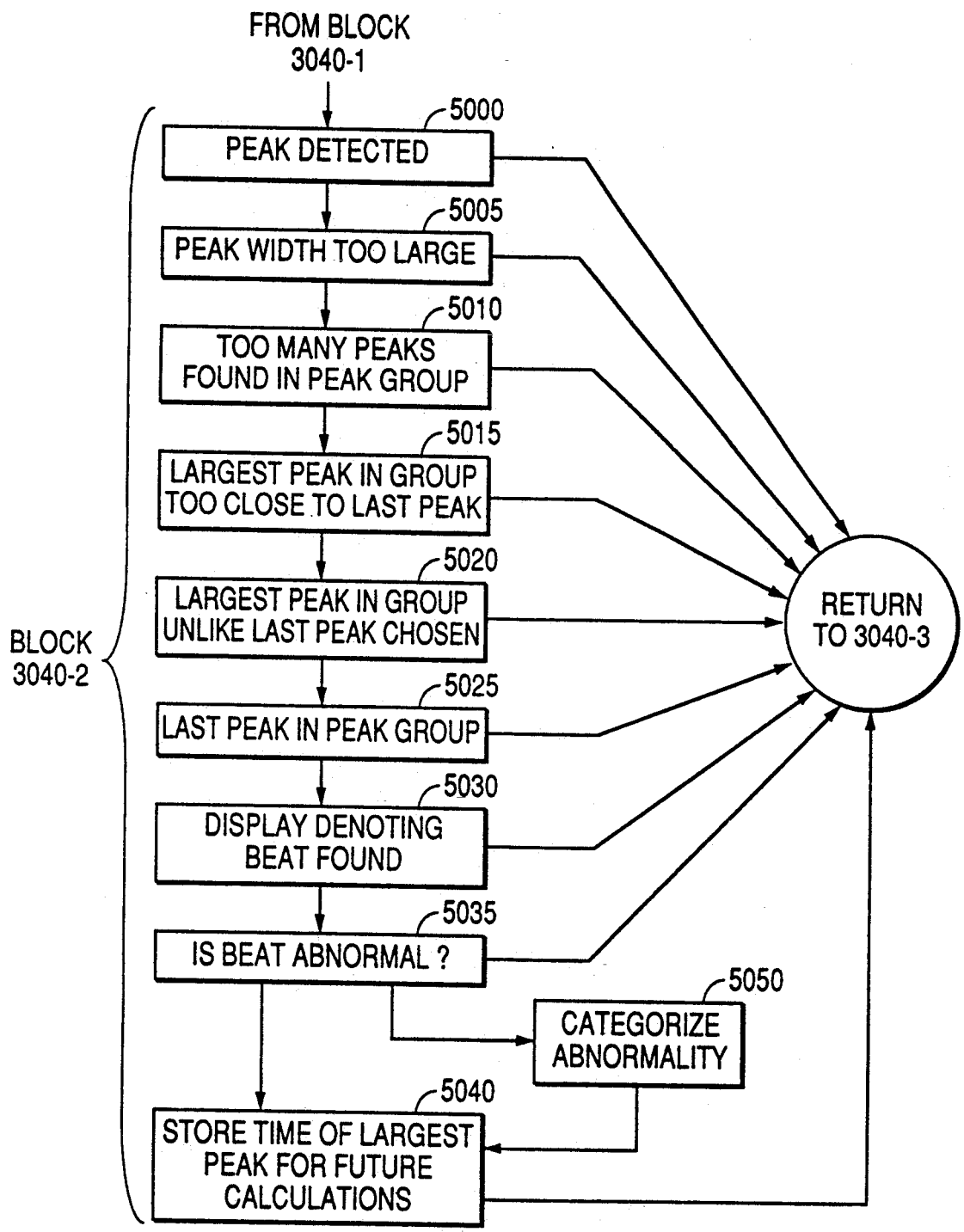
FIG. 5 describes specifically the beat detection algorithm of Block 3040-2 which is enabled at the start of any autonomic nervous system test.

Referring now to FIG. 5, there is shown a detailed schematic of Beat Detection Block 3040-2 from FIG. 4. After receiving the message from Block 3040-1 that the audiovisual portion has begun, the program checks for the presence of peaks in Block 5000. If peaks are detected, the signal peaks are checked to make sure they are of sufficient amplitude which may be either positive or negative deflections. Peaks are also checked for frequency. If the peak amplitude or peak rate average falls above or below a predetermined value, the program exits Beat Detection Block 3040-2 and continues with the next step 3040-3 of the RUN Test Block 3040. If peak signal is valid, the width of the peak is measured in Block 5005. If the Peak width exceeds a predetermined width, the program exits the Beat Detection Block and returns to 3040-3 as above. If the peak width is within an acceptable range, the program proceeds to 5010 where the number of peaks are counted within each peak width. If too many peaks are detected within the acceptable peak width, the program exits the Beat Detection Block and returns to 3040-3 as above. If the number of peaks are within the acceptable range of peaks for any given peak width, the program advances to 5015. The distance between each peak group is calculated. If the largest peak among the peak group is too close to the last detected peak, the program exits the Beat Detection Block and returns to 3040-3. If the peaks occur at a distance that correlate to the inherent physiological capabilities of the heart, the program proceeds to 5020. A comparison is made between one peak and the next to make certain that the peaks are a manifestation of heart activity and not just random noise. If consecutive peaks are dissimilar, the program exits the Beat Detection Block and returns to 3040-3 as above. If the peaks are similar, the program continues on to Block 5025 to determine whether the last peak in the group has been detected. This completes the discriminating steps of defining an ECG generated by the heart of a patient versus a signal originating from a source other than the human heart. When the last peak has been found, an audiovisual message is displayed denoting that a beat was found in Block 5030. Once it has been decided that the ECG signal is a beat, further analysis is performed to define whether the QRS is a "normal" beat or an "abnormal" beat in Block 5035.

Upon entry to the HIGH LEVEL BEAT DETECTION routine, the routine continues to make an analysis of both the peak itself and the peak cluster in order to refine the beat profile. The beat is checked for prematurity and width. If the beat does not exceed the prematurity and width criteria, the program proceeds to Block 5040 where the time of the largest peak is stored for future calculations. If the beat exceeds the prematurity and width criteria, the program branches to Block 5050 where the type of abnormality is determined. Block 5050 is described in more detail in FIG. 5. Once the abnormal beat is classified, the program returns to Block 5040 where the time and type of abnormal beat is logged and stored. The program then returns to Block 3040-3.

Figure 7:
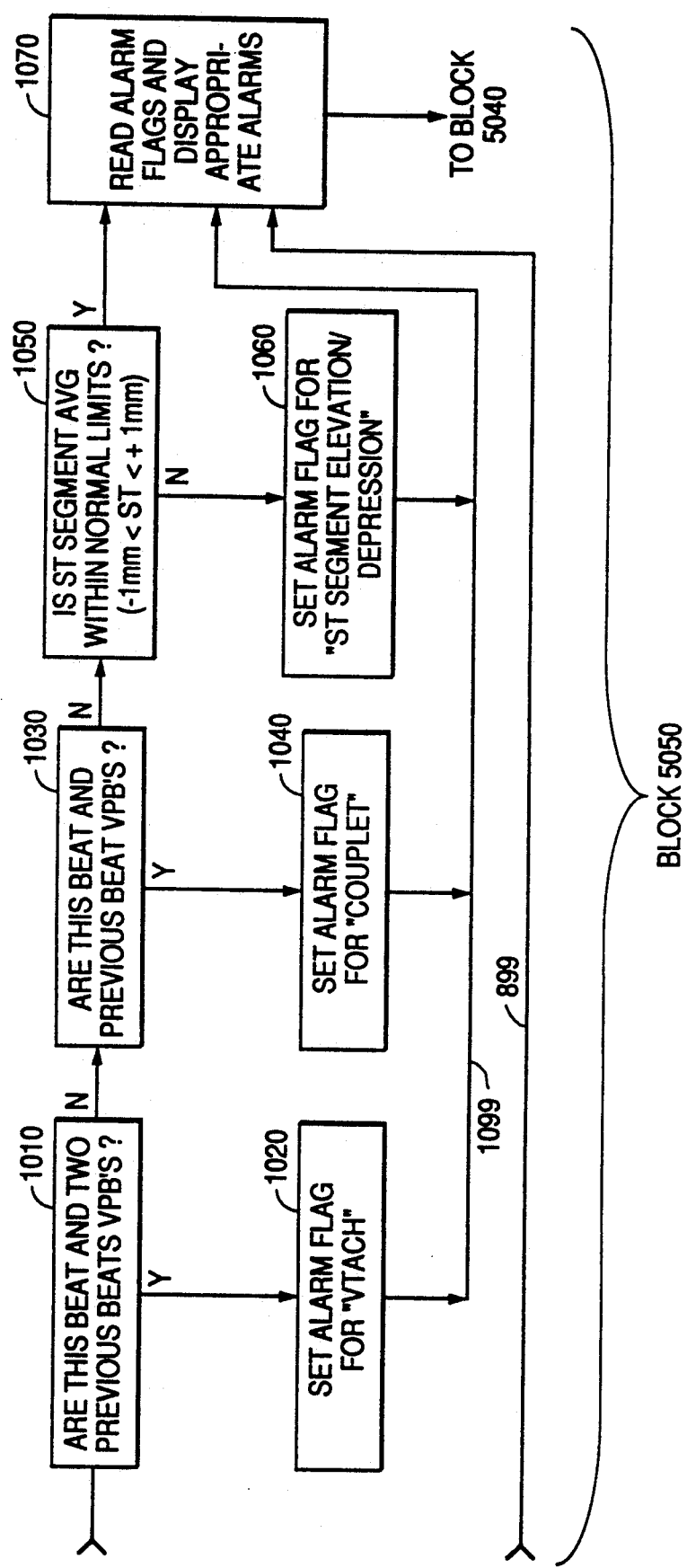

FIG. 6 and some of its corresponding descriptions have been reproduced from U.S. Pat. No. 4,679,144 to Cox et al who co-invented this new invention. This portion of the program describes abnormal beat detection and analysis. Specifically Block 510 "determines if the previous beat was a suspected VPB." If not, the program proceeds to FIG. 7 via line 118 for further analysis. "If the previous beat was a suspected VPB, the compensatory interval is calculated for the purpose of checking for the presence of a compensatory pause" in Block 520 "which would indicate that the suspected VPB was a true VPB. The current average pulse interval is added to the time at which the QRS complex preceding the suspected VPB is known to have occurred. This result represents a point in time at which a normal beat following a VPB would fall if a compensatory pause were present. If the current beat's time diverges from the calculated time by more than ±12.5% of the current average pulse interval, a compensatory pause is not indicated. The foregoing procedure is repeated three additional times with the average pulse interval being added to the previously calculated compensatory interval each time. This procedure allows for the verification of interpolated VPBs as well as the possibility of verification of VPBs which are followed by "undetected" QRS complexes. If no verification can be made by the end of the fourth attempt," the program advances to FIG. 7. "If verification is possible, the program proceeds to Block 530 where the suspected VPB is labelled as a confirmed VPB". The routine advances to Block 1010 in FIG. 7 (corresponds to FIG. 10 in U.S. Pat. No. 4,679,144) "where the logic looks at the results of the analysis performed for the current beat and the last two beats to determine whether all three beats exhibit VPB characteristics. If they do, the analyses move to Block 1020 where an alarm flag is set for a condition indicative of Ventricular Tachycardia, and this information is sent to Alarm Block 1070 via line 1099. If the three beats examined at Block 1010 do not exhibit VPB characteristics, the analyses proceed to Block 1030 where the results of the analyses performed for only the current beat and the last beat are examined. If the logic determines that for both beats VPB characteristics were exhibited, the analyses move to Block 1040 where an alarm flag is set for a condition known as "COUPLET" and an appropriate signal is passed to Block 1070 via line 1099; otherwise the analyses move to Block 1050 where the logic determines if the ST segment average is within acceptable limits. These limits are empirical values determined for any beat as a function of the isoelectric portion of the PQRST waveform associated with that beat." A check is made to insure that the beat has a 64 millisecond segment with at least 48 milliseconds of slope equal to or greater than 0.1 millimeter per millisecond. If the beat does not meet these criteria there is no further attempt to find an onset of J Point and instead the program proceeds to Block 1070. If, however, the beat meets the preliminary check for the presence of an ST segment, the isoelectric amplitude of the beat is calculated in the following manner: the amplitude of the beat is sampled at a minimum of four points prior to the onset time of the defined QRS portion of the beat. These points are then averaged to arrive at the isoelectric value. In the following operation the J Point is located. The J Point is defined for these purposes as the terminal point of the QRS complex wherein the active slope ceases. The J Point is in turn used to determine the position and amplitude of the ST Segment. A check is made on whether the segment occurs within an acceptable limit from the end of the beat. If so, the ST segment is tested to determine if it occurs within an acceptable limit from the onset of the beat. If the location of the ST segment falls within acceptable limits, the segment is tested for the following: does it follow the last peak of the beat?; is the segment amplitude within an acceptable limit from the isoelectric line as determined above?; and, is the segment followed by period of quiet slope having less than 0.1 millimeter of change in amplitude per millisecond?. "If the measured ST segment value falls within the limits, the logic proceeds to Block 1070. If the measured ST segment value falls outside the limits, the logic moves to Block 1060 where an alarm flag is set to reflect either a condition for "ST SEGMENT DEPRESSION" or "ST SEGMENT ELEVATION", and a signal corresponding to the condition detected is sent to alarm Block 1070 via line 1099."

"Block 1070, which receives information passed through Block 1050 from line 1099 and from line 899, then reads the alarm flags set and displays alarms corresponding to the various detected conditions of the device and the patient", if alarms are enabled. "In addition, Block 1070 updates the stored counts for VPBs, couplets, ventricular tachycardia and their duration, as well as the total ST segment duration." The logic then proceeds to Block 5040.

Figure 8:
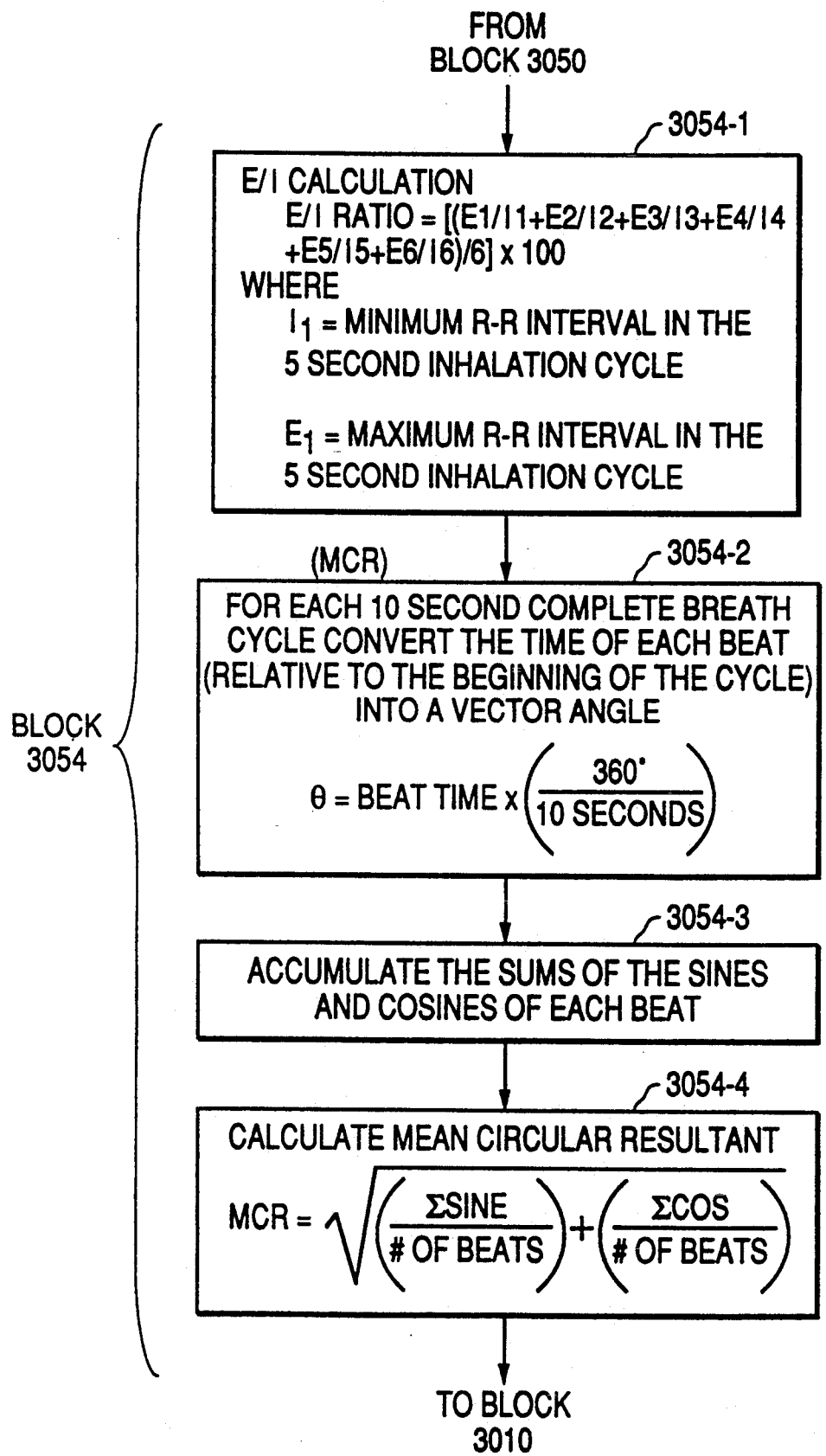
FIG. 8 shows the procedure for calculating the Expiratory/Inspiratory Ratio and Mean Circular Resultant at the completion of an error-free autonomic nervous system test.

Regardless of the categorization of the abnormal beat or the level of ST depression, the time of the largest peak is stored along with the abnormal beat label for future calculations in Block 5040. The accurate identification of abnormal beats and the time of their occurrence is critical when calculating an ANS test result so that R—R intervals in which at least one beat is abnormal will not be included in the calculation. An ANS test result can be skewed if abnormal beats were included. FIG. 8 shows a detailed schematic of Block 3054 which is a multi-purpose calculating and storing box for both the raw and computed data obtained during each ANS test. Specifically, the calculation of the Expiratory/Inspiratory Ratio, referred to as E/I Ratio, and the Mean Circular Resultant, referred to as MCR, is shown. In Block 3054-1, the start time for each of the six inhalation and exhalation cycles relative to the start time of the ANS test are calculated. The first beat for each cycle is located. The minimum heart beat interval, referred to as the R—R interval, for inhalation and the maximum R—R interval for exhalation are located for each breathing cycle comprised of one inhalation followed by one exhalation. The six minimum intervals are then added together and the six maximum intervals are summed. The sum of the minimum intervals is then divided by the sum of the maximum intervals and the quotient is multiplied by "100" to derive the E/I Ratio.

If the MCR option has been selected, the Mean Circular Resultant will begin to be calculated in Block 3054-2. The time of each beat is converted to an angle relative to its displacement from the beginning of the 10 second respiration cycle, comprised of one inhalation and one exhalation, in which the beat is contained. Sine and cosine for each "beat angle" are computed in Block 3054-3 and running sine and cosine sums are accumulated. The Mean Circular Resultant is then calculated in Block 3054-4 by the formula: MCR=the square root of ((the sum of the sines divided by the number of beats) squared plus the (sum of the cosines divided by the number of beats) squared). Upon completion the program returns to the Main Menu 3010.

Figure 9:
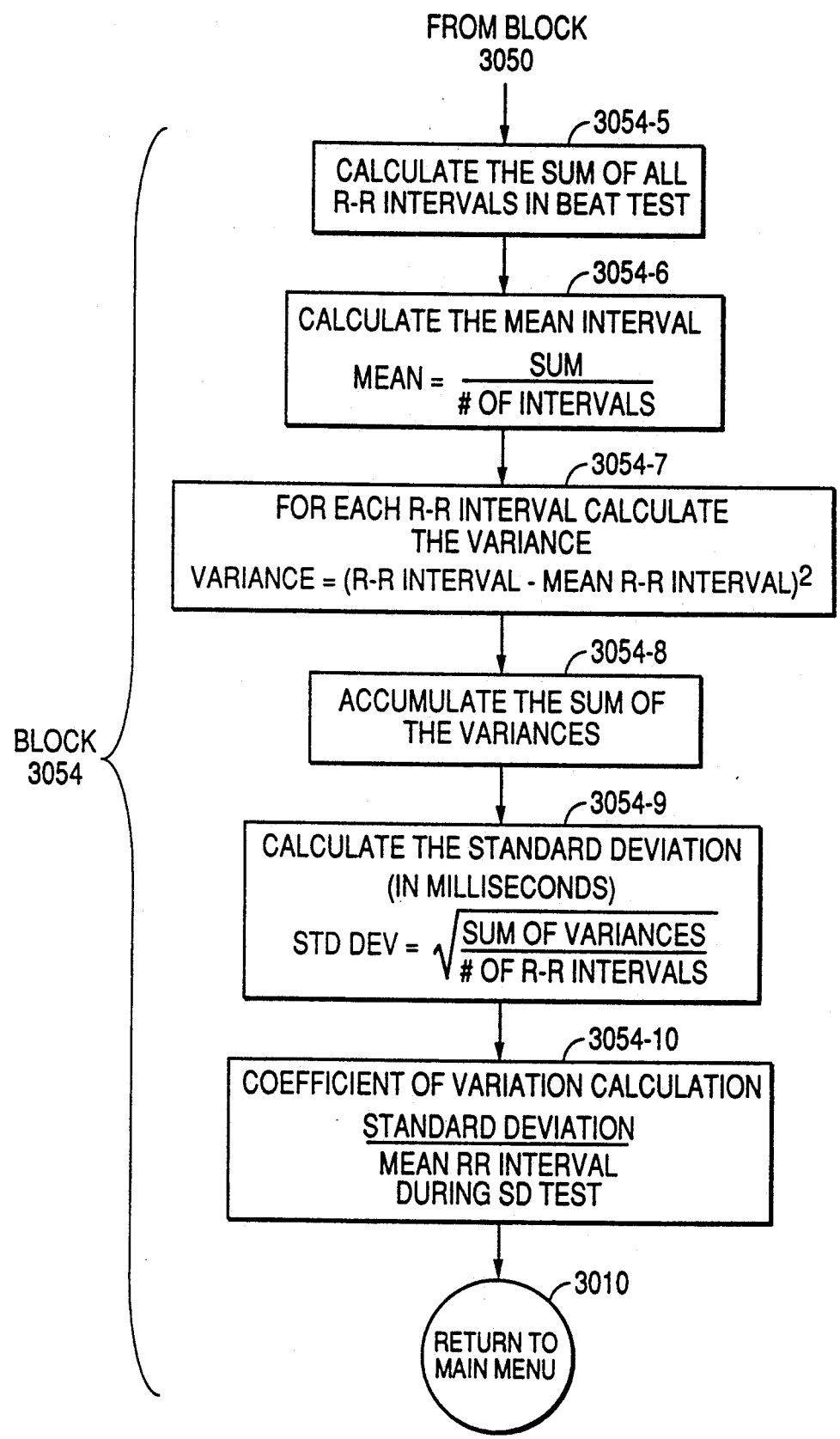
FIG. 9 shows the procedure for calculating the Standard Deviation and Coefficient of Variation at the completion of an error-free autonomic nervous system test.

FIG. 9 depicts a detailed schematic of Block 3054 of the process for calculating two more ANS test results: Standard Deviation and Coefficient of Variation. The Standard Deviation is calculated by first summing all R—R intervals in Block 3054-5. The Mean Interval is then calculated in Block 3054-6 by the formula: Mean Interval=(the sum of all R—R intervals divided by the number of intervals). In Block 3054-7, the Variance for each R—R interval is calculated using the formula: Variance=(the R—R interval —the Mean R—R interval) squared. The Variances thus derived are added together in Block 3054-8, and the Standard Deviation is calculated in Block 3054-9 according to the formula: STD DEV=the square root of (the sum of the variances divided by the number of R—R intervals). The Standard Deviation is then converted to milliseconds by multiplying the Standard Deviation by the quotient of 1000 divided by 256. The Coefficient of Variation, which is a byproduct of Standard Deviation, divides the Standard Deviation value from Block 3054-9 by the mean R—R interval during the performing of the predetermined breathing regimen. The program returns to the Main Menu 3010.

Figure 10:
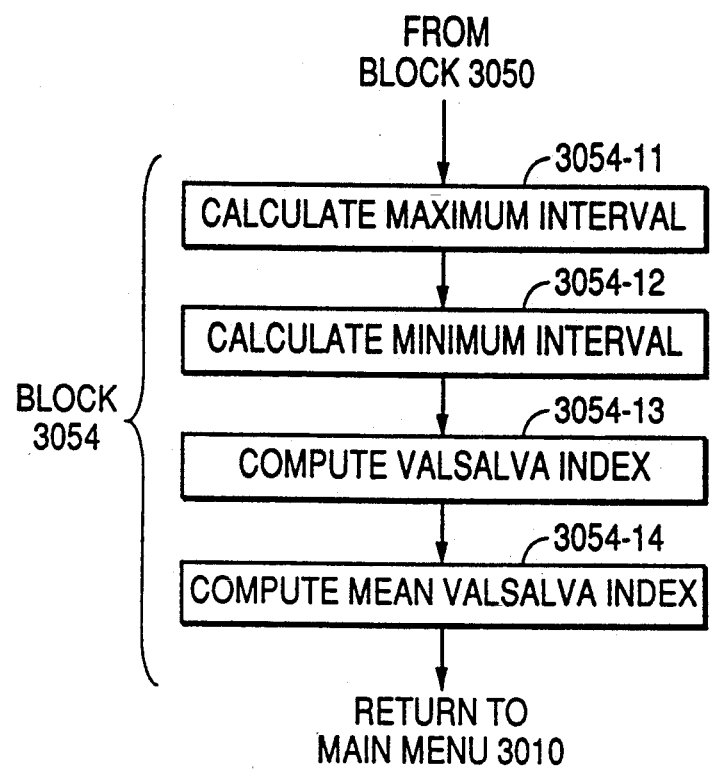
FIG. 10 shows the procedure for computing the Valsalva Index at the completion of an autonomic nervous system test.

FIG. 10 details the process for computing the Valsalva Index in Block 3054. In Block 3054-11, the beat times during the first 20 seconds of the predetermined paced breathing regimen are scanned to find the maximum heart beat interval. The maximum interval is then checked to see if it is the first interval of the first twenty seconds of the predetermined breathing regimen. If it is the first interval, the average must be calculated separately where the length of the first heart beat interval is added to the length of the second heart beat interval which in turn is added to the length of the third heart beat interval, and the sum is divided by three to yield an averaged maximum heart beat interval. A check is made to see if the maximum interval is the final interval of the forced exhalation cycle of the first twenty seconds. The final interval must also be averaged separately to find the maximum: the length of the last heart beat interval of the twenty second breathing regimen is added to the length of the second to last heart beat interval which in turn is added to the third to last heart beat interval. The sum is then divided by three to yield the final three beat averaged maximum. If the maximum interval during the entire twenty second breathing regimen was neither the first nor the last interval the three beat maximum average is calculated where: the length of the maximum heart beat interval is added to the length of the previous heart beat interval which is in turn added to the length of the following heart beat interval and the sum is divided by three. The maximum of the three averaged maximum values becomes the Valsalva Average Maximum.

The same series of operations is duplicated for the Valsalva Minimum in Block 3054-12 beginning with a scan for the minimum interval from the 60 second part of the predetermined breathing regimen consisting of non-paced relaxed breathing following the twenty seconds of forced exhalation. The Valsalva Index is then computed for the first Valsalva test in Block 3054-13. If more than one Valsalva test was performed, the Valsalva Indices for each test are summed, and then divided by the number of Valsalva tests performed to derive the Mean Valsalva Index. The program then returns to Main Menu 3010.

Figure 11:
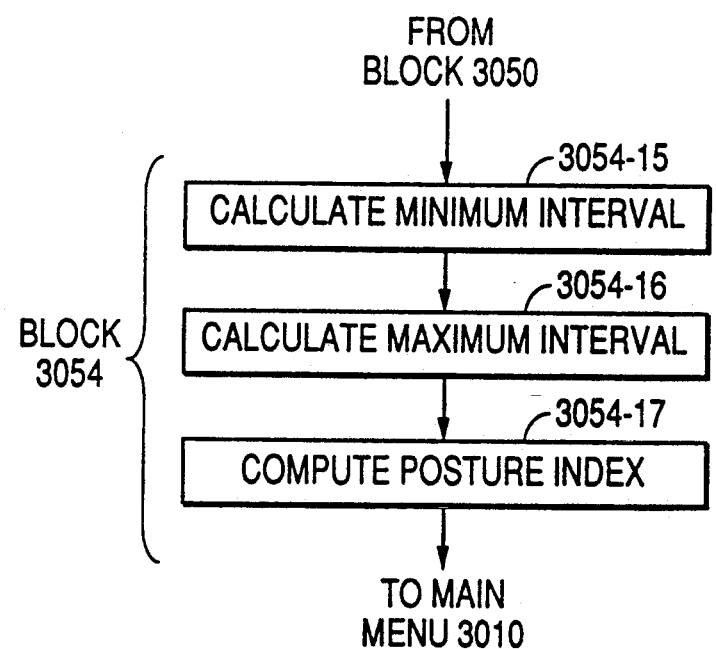
FIG. 11 shows the procedure for calculating the Posture Index.

FIG. 11 describes the Posture Index calculation in more detail than Block 3054. In Block 3054-15, the minimum heart beat interval is determined from a specific range of heart beat intervals between intervals 11 through 19 since this is the period of time in which the heart demonstrates the minimum intervals upon standing from a lying down position. In Block 3054-15, the maximum interval is then calculated between the 25th and 35th heart beat interval after standing. The maximum interval is then divided by the minimum interval to derive the Posture Index in Block 3054-17. The program then returns to Main Menu 3010.

What is claimed is:

1. Automated apparatus for monitoring heart beat signals generated by the heart of a patient to whom it is attached, comprising:
   means for performing continuous real-time analysis of said heart beat signals derived from said patient,
   means for storing one or more normative data bases for automated correlation of test result to age-matched values,
   means for recognizing normal and abnormal beats,
   means for diagnosing each of said abnormal beats,
   means for providing audio-visual signals to the patient to instruct said patient in at least one predetermined physical regimen, whereby the patient may perform said at least one predetermined physical regimen without any additional prompting or instruction, and
   means for outputting the results of said analysis.

2. The apparatus of claim 1, wherein said means for outputting results includes means adapted to cooperate with external data handling means.

3. The apparatus of claim 2, wherein said means adapted to cooperate comprises optical emitter means adapted to be coupled to an optical receiver, whereby said results can be output from said automated apparatus to said external data handling means, and said external data handling means may comprise a printer, a modem, a computer, or other external data handling means.

4. The apparatus of claim 2, wherein said means for outputting results further comprises display means, and wherein said display means is also the visual portion of said audio-visual signal providing means.

5. The apparatus of claim 1, wherein said predetermined physical regimen is a predetermined paced breathing regimen.

6. The apparatus of claim 1, wherein said predetermined physical regimen is a predetermined posture regimen.

7. A computer implemented method of performing a test of a patient's autonomic nervous system comprising monitoring every beat of the heart of said patient to detect and correlate variations in heart functioning during a predetermined physical regimen to autonomic nervous system functioning, comprising the steps of:
   attaching sensing means to the patient to sense the heart beat of said patient,
   using the output signal of said sensing means to produce heart beat signals,
   analyzing said heart beat signals,
   determining from said analysis of said heart beat signals if each said signal is representative of one of a normal or abnormal heart beat or an artifact,
   issuing continuous audio-visual instructions to the patient to guide the patient in performing said predetermined physical regimen,
   storing data during the patient's performance of said predetermined physical regimen,
   performing all of the aforesaid steps in a predetermined quantity based on said heart beat signals only to thereby define a test,
   correlating the results of said test with age-matched values to accurately assess the extent of automatic nervous system function, and
   outputting the results of said test upon conclusion of said test.

8. The method of claim 7, wherein said predetermined physical regimen is a predetermined paced breathing regimen.

9. The method of claim 7, wherein said predetermined physical regimen is a predetermined posture regimen.

10. The method of claim 7, wherein said outputting of results step includes outputting a portion of said results.

11. The method of claim 7, and performing all of said steps continuously during the running of each said test.

12. The method of claim 7, wherein said test is performed because said patient is at least suspected of having at least one of diabetes, a predisposition to sudden death, alcohol addiction, coronary artery disease, muscular dystrophy, parkinsonism, HIV infection, Shy-Drager syndrome, impotence, sleep apnea, toxic neuropathies, and any other disease which affects the autonomic nervous system.

13. A computer implemented method of evaluating autonomic nervous system functioning comprising the steps of:
   instructing a patient whose autonomic nervous system is being evaluated to perform a predetermined physical regimen,
   sensing each beat of the heart of said patient,
   determining by analyzing said heart beats, whether or not each said heart beat is representative of a normal or abnormal heart beat, producing a signal corresponding to each said sensed heart beat, calculating the time from a selected point on one signal to the corresponding point on the next succeeding signal, correlating said predetermined physical regimen with said calculating step, storing raw data from said steps of producing, calculating, and correlating said signals, correlating the results of said test with age-matched values to accurately assess the extent of automatic nervous system functioning, and providing at least one autonomic nervous system test result substantially instantaneously based on said calculating, correlating, and storing steps.

14. The method of claim 13, wherein said predetermined physical regimen is a predetermined paced breathing regimen.

15. The method of claim 13, wherein said predetermined physical regimen is a predetermined posture regimen.

16. The method of claim 13, and performing said instructing step for a plurality of times.

17. The method of claim 13, and the additional step of classifying each said sensed heart beat as normal or abnormal.

18. The method of claim 17, and the further steps of determining an autonomic nervous system test result based on said sensed normal beats only comprising:

identifying said selected point on one said sensed heart beat and the corresponding selected point on the next succeeding said sensed heart beat, determining if said next succeeding such sensed heart beat is normal, repeating said identifying step if said next succeeding such sensed heart beat is not normal as determined by said determining step, and calculating the time between said corresponding selected points only if both said succeeding sensed heart beats are normal, whereby the accuracy of said autonomic nervous system test result based on said calculating step is increased due to the inclusion of normal beats only in said calculating step.

19. The method of claim 17, and the further step of identifying each beat classified as abnormal in said last mentioned classification step as an abnormal beat originating from the heart of said patient or as an abnormal beat originating from a source other than the heart of said patient.

20. The method of claim 13, and performing said producing step to produce an EKG signal, and selecting said selected point on said succeeding signals from the group consisting of the R-wave, Q-wave, QS-wave, P-wave, T-wave or any other point on said EKG signals.

21. The method of claim 13, wherein said autonomic nervous system test result is the Standard Deviation and the further steps of:

determining the mean time of said calculating step during predetermined paced breathing regimen based on said instructing step, and relating all of said times derived from said calculating step to said mean time to provide said Standard Deviation indicative of said autonomic nervous system function.

22. The method of claim 21, wherein the performance of said relating step is automated and substantially instantaneous.

23. The method of claim 13, wherein said autonomic nervous system test result is the Mean Circular Resultant and the further steps of:

identifying the time of onset of each cycle of breathing comprising said predetermined physical regimen, calculating the time between the occurrence of said selected point of each said sensed heart beat relative to said time of onset of each said cycle, converting said times produced in said calculating step to vectors comprised of X and Y components, repeating said converting step for each said cycle, computing a single average vector of said X and Y components for all said cycles, and determining a Mean Circular Resultant indicative of said autonomic nervous system function.

24. The method of claim 23, wherein the performance said determining step is automated and substantially instantaneous.

25. The method of claim 13, wherein said autonomic nervous system test result is the Valsalva Index and the further steps of:

identifying the maximum time of said calculating step during said predetermined physical regimen based on said instructing step, identifying the minimum time of said calculating step during a predetermined time following the completion of said predetermined physical regimen based on said instructing step, and correlating said maximum and minimum times to provide said Valsalva Index indicative of said autonomic nervous system function.

26. Automated apparatus for editing a calculated test result which has been initially based on automatically selected portions of raw data derived from monitoring of heart beat signals during the performance of at least one predetermined physical regimen, comprising:

means for outputting said calculated test result, means for storing one or more normative data bases for automated correlation of test result to age-matched values, means for outputting automatically selected heart beat intervals selected from said raw data which were used to calculate said test result, means for outputting said raw data, means for inputting manually selected heart beat intervals selected from said raw data that differ from said automatically selected heart beat intervals, means for recalculating said test result based on said manually selected heart beat intervals, and means for outputting said recalculated test result, whereby said calculated test result is edited.

27. The apparatus of claim 26, wherein said means for outputting said test result further includes means adapted to cooperate with external data handling means.

28. The apparatus of claim 26, wherein said means adapted to cooperate comprising optical emitter means coupled to an optical receiver, whereby said test results can be output from said apparatus to said external data handling means, and said external data handling means may comprise a printer, a modem, or a computer.

29. The apparatus of claim 26, wherein said automated apparatus is self-contained and portable.

30. The apparatus of claim 26, wherein said predetermined physical regimen is a predetermined paced breathing regimen.

31. The apparatus of claim 26, wherein said predetermined physical regimen is a predetermined posture regimen.

32. An automated apparatus for evaluating the function of a patient's autonomic nervous system comprising:
means for storing one or more normative data bases for automated correlation of test result to age-matched values,
means for sensing signals,
means for determining if said sensed signals are representative of a heart beat or an artifact,
means for classifying said signals representative of a heart beat as normal or abnormal,
means for performing continuous real-time analysis of said signals derived from said patient,
means for providing audio-visual signals to said patient to instruct said patient in at least one predetermined physical regimen,
means for correlating said signals with said at least one predetermined physical regimen,
means for automatically calculating test results based on said correlating step for evaluating said function of the autonomic nervous system of said patient,
means for outputting said test results,
means for outputting said signals,
means for interfacing said outputting of said test result with external data handling means,
means for editing said test result,
means for inputting portions of said signals for automatic recalculation of said test result, and
display means forming part of all of said means for providing audio-visual signals, all of said means for outputting, said means for inputting, and said means for editing.

33. The apparatus of claim 32, wherein said predetermined physical regimen is a predetermined paced breathing regimen.

34. The apparatus of claim 32, wherein said predetermined physical regimen is a predetermined posture regimen.

35. A computer implemented method of evaluating autonomic nervous system functioning comprising the steps of:
instructing a patient whose autonomic nervous system is being evaluated to perform a predetermined posture regimen,
sensing each beat of the heart of said patient,
determining by analyzing said heart beats, whether or not each said heart beat is representative of a normal or abnormal heart beat,
producing a signal corresponding to each said sensed heart beat,
calculating the time from a selected point on one signal to the corresponding point on the next succeeding signal,
correlating said predetermined posture regimen with said calculating step,
storing raw data from said steps of producing, calculating, and correlating said signals,
correlating the results of said test with age-matched values to accurately assess the extent of autonomic nervous system functioning, and
providing at least one autonomic nervous system test result substantially instantaneously based on said calculating, correlating, and storing steps.

36. The method of claim 35, wherein said predetermined posture regimen comprises standing and lying down maneuvers.

37. The method of claim 35, wherein said predetermined posture regimen is 10 seconds of standing, then 60 seconds of lying, followed by 60 seconds of standing.

38. The method of claim 36, wherein said standing maneuver is performed for at least 30 beats of the heart.

39. The method of claim 35, wherein said autonomic nervous system test result is the Posture Index and the further steps of:
identifying the maximum time of said calculating step,
identifying the minimum time of said calculating step,
correlating said maximum and minimum times using an established formula to produce said Posture Index indicative of said autonomic nervous system function.

40. The method of claim 39, wherein said last mentioned correlating step is performed automatically and substantially instantaneously.

41. A computer implemented method of editing at least one autonomic nervous system test result which has been previously calculated from automatically selected heart beat intervals of recorded raw data, comprising the steps of:
providing an output means,
outputting at least a portion of said automatically selected heart beat intervals,
outputting at least a portion of said recorded raw data,
identifying said portion of recorded raw data that differs from said automatically selected heart beat intervals for recalculating said test result,
providing input means,
inputting said portion of recorded data identified in identifying step,
recalculating said test result based on said data input in said inputting step,
correlating the results of said tests with age-matched values to accurately assess the extent of autonomic nervous system functioning, and
outputting said recalculated test result,
whereby the accuracy of said test result is increased due to the said method of editing by an operator.

42. The method of claim 41, wherein said recalculating step is performed automatically and substantially instantaneously.

43. The method of claim 41, and repeating of said steps of identifying, providing, inputting, recalculating and outputting until said test result is acceptable to said operator.

* * * * *

UNITED STATES PATENT AND TRADEMARK OFFICE
CERTIFICATE OF CORRECTION

PATENT NO. : 5,299,119
DATED : March 29, 1994
INVENTOR(S) : Kraf et al

It is certified that error appears in the above-indentified patent and that said Letters Patent is hereby corrected as shown below:

<u>IN THE DRAWINGS</u>:

In the drawings, Sheet 7, Fig. 8, block 3054-1, the second occurrence of "INHALATION" should be -- EXHALATION --.

Signed and Sealed this

Nineteenth Day of July, 1994

Attest:

BRUCE LEHMAN

*Attesting Officer*     *Commissioner of Patents and Trademarks*